United States Patent [19]

Sullivan

[11] Patent Number: 5,330,430
[45] Date of Patent: Jul. 19, 1994

[54] RETRACTABLE SYRINGE APPLICATOR

[76] Inventor: Robert J. Sullivan, 15 Floramar, Rancho Santa Margarita, Calif. 92688

[21] Appl. No.: 163,299

[22] Filed: Dec. 6, 1993

[51] Int. Cl.⁵ .............................................. A61M 5/20
[52] U.S. Cl. .................................. 604/134; 604/195; 604/198
[58] Field of Search ............... 604/110, 187, 192, 198, 604/218, 132–137, 263, 232, 195

[56] References Cited

U.S. PATENT DOCUMENTS

| | | | |
|---|---|---|---|
| 3,880,163 | 4/1975 | Ritterskamp | 604/136 |
| 4,507,117 | 3/1985 | Vining et al. | 604/196 |
| 4,631,057 | 4/1986 | Mitchell | 604/198 |
| 4,642,099 | 2/1987 | Phillips et al. | 604/136 |
| 4,787,891 | 11/1988 | Levin et al. | 604/187 X |
| 4,820,275 | 4/1989 | Haber et al. | 604/198 |
| 4,931,040 | 6/1990 | Haber | 604/110 |
| 5,017,187 | 5/1991 | Sullivan | 604/110 |

*Primary Examiner*—John D. Yasko

[57] ABSTRACT

A combination retractable syringe and injector enclosure are disclosed. A hypodermic syringe is placed into the injector enclosure and attached to a spring-loaded plunger. The plunger terminates in a tubular case that houses a coil spring and extends out from one end of the injector enclosure. An empty syringe may be filled by loading the injector with the empty syringe, engaging the plunger with the empty syringe, positioning a canula or needle of the syringe for collecting a fluid, and then withdrawing the case and plunger from the end of the injector enclosure. This causes the syringe to pull fluid from the canula and into the body of the syringe. In an alternate use, a fluid in a full syringe is dispensed by loading the injector enclosure with the full syringe, engaging the plunger with the full syringe, positioning the canula for injection, and then pushing the case into the injector enclosure. Upon the complete dispensing of the fluid within the syringe, two disengaging means within the injector enclosure come into contact with two corresponding locking means within the enclosure, thereby freeing the spring within the case to retract the syringe completely into the injector enclosure. As such, the canula is automatically withdrawn from the injection site and retained safely within the injector enclosure. The entire device is then safely discarded.

9 Claims, 3 Drawing Sheets

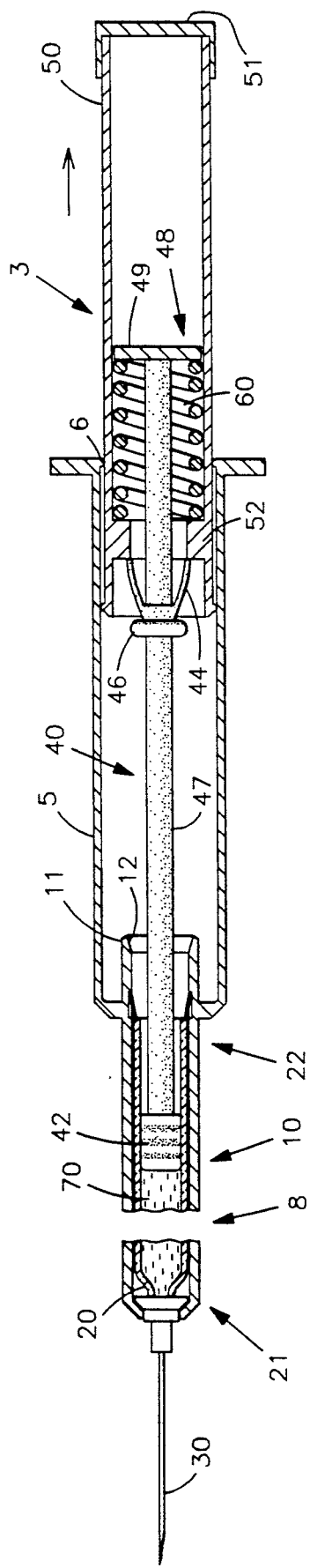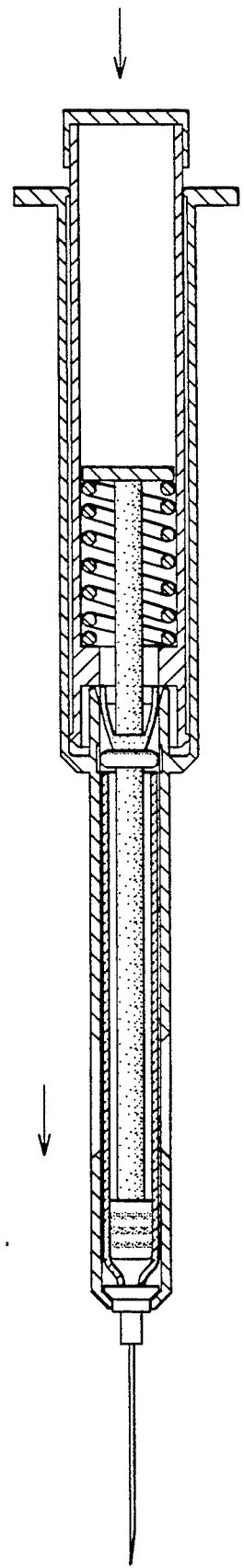
FIG 2
FIG 3

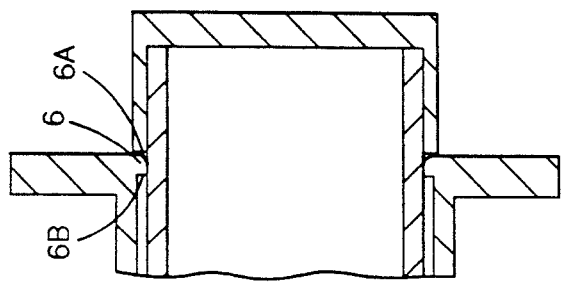
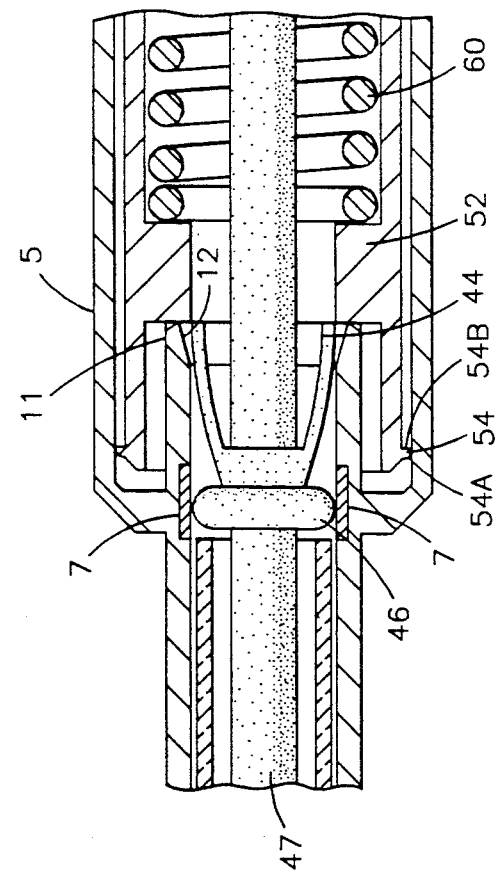
FIG 4
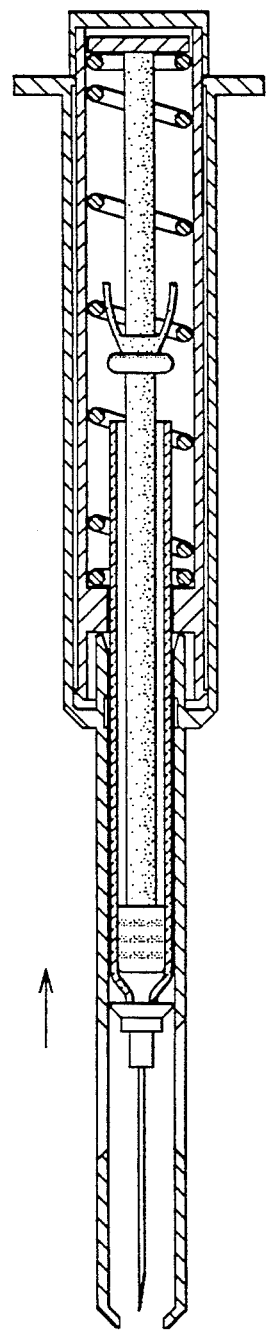
FIG 5

RETRACTABLE SYRINGE APPLICATOR

FIELD OF THE INVENTION

This invention relates generally to retractable syringes, and, more particularly, is directed towards a retractable syringe that is used with pre-filled syringe cartridges.

BACKGROUND OF THE INVENTION

Pre-filled syringe cartridges are becoming more common because many medications, to be effective and even safe, require precise mixing at a well controlled mixing location, such as in a pharmaceutical manufacturing location. In a typical hospital or doctor's office it is usually not possible to mix certain medications accurately enough, since such locations do not normally have, nor can afford, the proper and precise mixing equipment required. As such, it is increasingly necessary to use such pre-filled syringe cartridges. Typically, however, the syringe enclosures used with such pre-filled syringe cartridges are not capable of retracting the needle or canula into a protective enclosure for the purposes of avoiding inadvertent, and potentially harmful, needle sticks.

One syringe device currently available includes an enclosure for use with a pre-filled syringe cartridge of medicine. This type of device is taught in U.S. Pat. No. 4,820,275 to Haber at al. on Apr. 11, 1989. While such a device does provide for the spring-influenced retraction of the needle and syringe, such retraction does not occur automatically upon the complete dispensing of the fluid contents of the cartridge. As such, it is possible for the needle to be withdrawn from the patient after delivery of the medication and still be unsafely exposed to others. Further, withdrawal of the needle by the medical practitioner is required, and such manual withdrawal of the needle, if done slowly and with lateral movement, can cause pain to the patient. While such a device might be better suited for dental work, it clearly has certain drawbacks when applied to more general medical fields.

Clearly, then, there is a need for an applicator device for use with a pre-filled syringe cartridge that, upon complete delivery of the contents of the cartridges, automatically retracts the syringe and needle safely into an inaccessible enclosure. Such a needed device could be used both for drawing fluid into the syringe, such as from a medicine bottle, and dispensing the fluid out of the syringe, such as while delivering an injection to a patient. Such a needed device would be relatively inexpensive to manufacture and easy to use. The present invention fulfills these needs and provides further related advantages.

SUMMARY OF THE INVENTION

The present invention is a combination retractable injector and injector enclosure. A hypodermic syringe is placed into the injector enclosure and attached to a spring-loaded plunger. The plunger terminates in a tubular case that houses a coil spring and extends from one end of the injector enclosure. The device may be used in either of two ways. First, an empty syringe may be filled by loading the injector with the empty syringe, engaging the plunger with the empty syringe, positioning a canula or needle for collecting a fluid, and then withdrawing the case and plunger from the end of the injector enclosure. This causes the syringe to pull fluid from the canula and into the body of the syringe. In an alternate use of the invention, a fluid in a full syringe is dispensed by loading the injector enclosure with the full syringe, engaging the plunger with the full syringe, positioning the canula for injection, and then pushing the case into the injector enclosure. Upon the complete dispensing of the fluid within the syringe, two disengaging means within the injector enclosure come into contact with two corresponding locking means within the enclosure, thereby freeing the spring within the case to retract the syringe completely into the injector enclosure. As such, the canula is automatically withdrawn from the injection site and retained safely within the injector enclosure. The entire device is then safely discarded.

A foremost advantage of the present invention is that upon completion of the injection the syringe canula or needle is automatically and safely withdrawn into the injector enclosure. Such retraction of the canula is accomplished quite quickly, which tends to minimize the pain often felt by a patient when a needle is being withdrawn. Further, the present invention is used with currently available pre-filled syringe cartridges. The present device embodies these advantages with as few as four separate parts, make such a device relatively inexpensive to manufacture. Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 2 is a full longitudinal cross-sectional view of the invention, illustrating a plunger and an inner case within the injector enclosure of the invention;

FIG. 3 is a full longitudinal cross-sectional view of the invention, illustrating the plunger as being fully depressed into the syringe body of the syringe;

FIG. 4 is a partial cross-sectional view of the invention, illustrating in more detail a first and second locking means and a corresponding second and first disengaging means of the invention; and FIG. 5 is a full longitudinal cross-sectional view of the invention, illustrating an uncompressed coil spring within the inner case and the syringe completely withdrawn into the injector enclosure.

DETAILED DESCRIPTION OF THE PREFERRED EMBODIMENT

Figure 1:
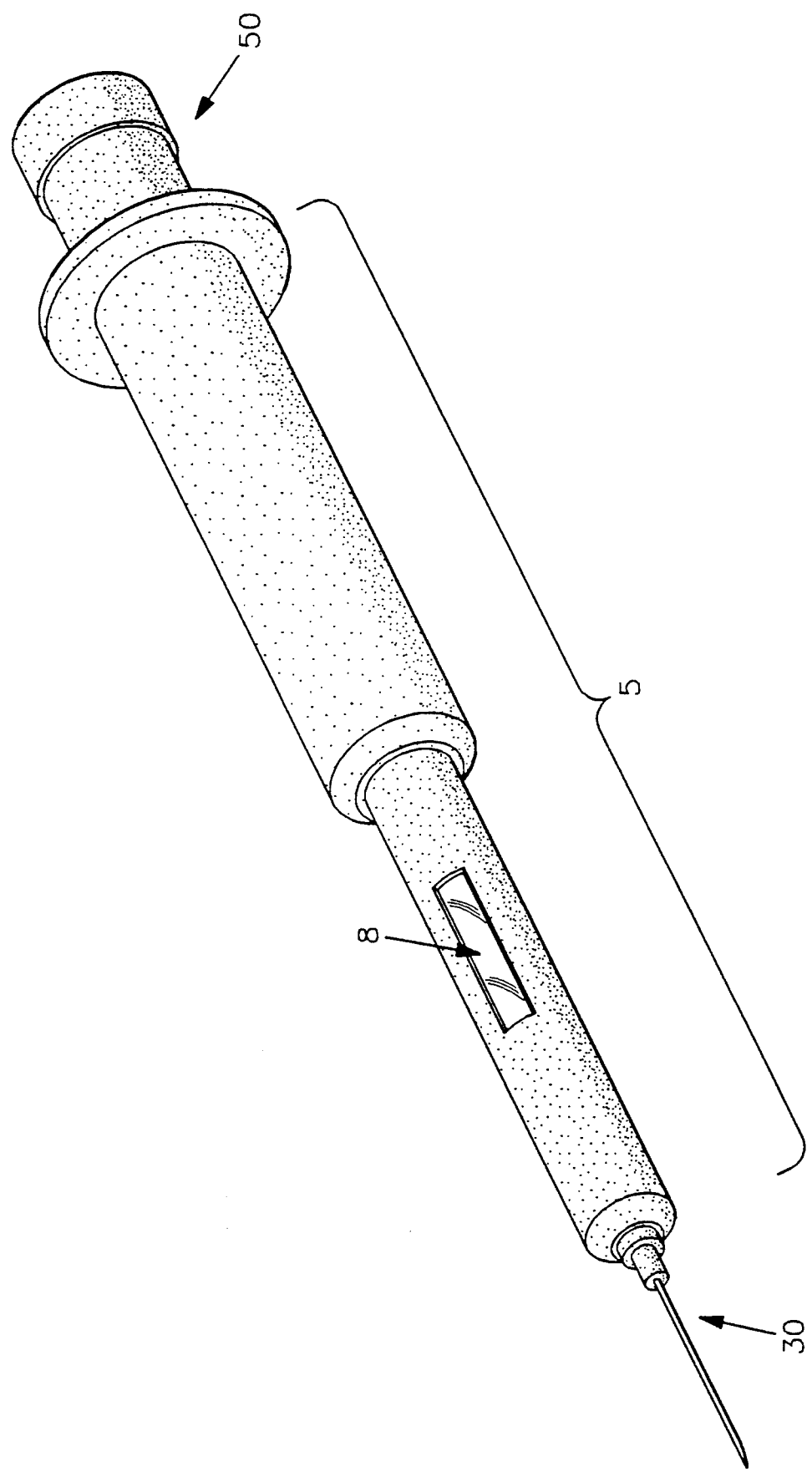
FIG. 1 is a perspective illustration of the invention, illustrating an injector enclosure with a finger opening therein, and a canula of a syringe protruding from an open end of the injector enclosure.

FIG. 1 shows a combination retractable injector 3 and injector enclosure 5. A hypodermic syringe 10 includes a cylindrical syringe body 20 that supports an axially mounted canula 30 at one end 21 thereof. The other end 22 of the syringe body 20 is open. The injector enclosure 5 and retractable injector 3 are preferably made from a rigid, transparent plastic material.

The retractable injector 3 includes a separable plunger 40 that is attached to sealing means 42 and is slidably engaged within the syringe body 20. The plunger 40 preferably includes a rod shaped element 47 that engages the sealing means 42 by a threaded screw means (not shown). The rod shaped element 47 further includes an outwardly biased first locking means 44, a first disengaging means 46, and a grasping and manipulating means 48, all extending from the open end 22 of the syringe body 20. The first locking means 44 is preferably a pair of opposed first tines disposed radially outwardly from the rod shaped element 47. The first disengaging means 46 is a coaxial annular torroidal element fixed to the rod shaped element 47 and extending outwardly therefrom. The grasping and manipulation means 48 is preferably a disk shaped element 49 fixed at the far end of the rod shaped element 47.

The retractable injector 3 further includes an open ended tubular inner case 50 providing an internal annular lip 52 having an opening for passing the syringe body 20 therethrough and for engaging the first locking means 44. The inner case 50 further provides a coil spring 60 coaxially engaged within the inner case 50 between the annular lip 52 and the grasping and manipulation means 48 of the plunger 40. As such, with the first locking means 44 engaged with the annular lip 52, the spring 60 is held in compression. The disk shaped element 49 is of a diameter for snug fit within the inner case 50 so as to compress the spring 60 by contacting one end of the spring 60. A cap 51 is included on the open end of the tubular inner case 50 for allowing manual grasping and rotating of the grasping and manipulation means 48, so that the rod shaped element 47 may be rotated for engaging the sealing means 42 of the syringe 10.

The injector enclosure 5 is of tubular construction and includes an inwardly biased second locking means 7, which is preferably a plurality of radially opposed second tines flexibly fixed to and radially inwardly extending from the injector enclosure 5 (FIGS. 2 and 4). The enclosure 5 operably engages the combination of the syringe 10 and the inner case 50 within the enclosure 5. The canula 30 and the inner case 50 extend from opposite ends of the injector enclosure 5 respectively. The second locking means 7 engages the other end 22 of the syringe body 20 for locking the syringe body 20 in place at a forward position 8 within the injector enclosure 5. As such, as the inner case 50 is drawn out of the enclosure 5, the plunger 40 is drawn through the syringe body 20 to fill the body 20 with an injection liquid 70.

The injector enclosure 5 further includes a second disengaging means 11 for forcing the first engagement means 44 to disengage the annular lip 52 of the inner case 50. The second disengaging means 11 is preferably an annular rim positioned coaxially with respect to the plunger 40 and having a conical interior surface 12. The first tines of the first disengaging means 44 are curved in extension for smooth contact with the rim. The injector enclosure 5 further includes at least one finger opening 8 therein for accepting a finger (not shown) in asserting finger pressure against the hypodermic syringe body 20 in order to prevent the body 20 from rotating when assembling the plunger 40 to the sealing means 42, such as by rotation of a screw thread on the plunger 40 (not shown).

The inner case 50 preferably includes an external annular lip 54, while the injector enclosure 5 includes an internal annular lip 6. The lips 54,6 are mutually engaged in a forced fit at the outset of insertion of the inner case 50 into the injector enclosure 5. The lips 54,6 touch at radiused annular lip surfaces 54A,6A for allowing the lips 54,6 to pass each other. Further, the lips each have flat annular surfaces 54B,6B for mutual contact in preventing the inner case 50 from being removed from the injector enclosure 5.

In one use of the device, wherein a fluid is to be collected, an empty syringe body 20 is attached to the plunger 40 and the syringe body 20 is engaged with the injector enclosure 5 in the forward position 8. The canula 30 is positioned for receiving the fluid, such as in a vein or in a vial of medication. The inner case 50 is then withdrawn, causing the plunger to be retracted from the syringe 10, wherein the fluid is drawn into the syringe body 20.

Alternatively, in another use of the device wherein a fluid is to be dispensed from the syringe 10, such as into a vein, the canula 30 is positioned for injecting. The inner case 50 is pressed into the injector enclosure 5, thereby driving the plunger 40 into the syringe body 20 for injecting the injection liquid (FIG. 3). When the first and second disengaging means 46,11 are brought simultaneously into contact with the second and first locking means 7,44, respectively, the syringe body 20 is disengaged from the forward position 8 within the injector enclosure 5 and the plunger 40 is disengaged from the annular lip 52 of the inner case 50. Consequently, the spring 60 drives the hypodermic syringe 10 fully into the injector enclosure 5 to conceal the canula 30 (FIG. 5).

While the invention has been described with reference to a preferred embodiment, it is to be clearly understood by those skilled in the art that the invention is not limited thereto. Rather, the scope of the invention is to be interpreted only in conjunction with the appended claims.

What is claimed is:

1. A combination retractable injector and injector enclosure comprising:

a hypodermic syringe including a cylindrical syringe body supporting an axially mounted canula at one end, the other end being open, and including a plunger slidably engaged within the body, the plunger having a sealing means, outwardly biased first locking means, first disengaging means, and a grasping and manipulation means, the LATTER extending from the open other end of the syringe body; and an open ended tubular inner case providing, an internal annular lip adapted for passing the syringe body therethrough, and for engaging the first locking means, the inner case further providing a coil spring coaxially engaged within the inner case between the annular lip and the grasping and manipulation means of the plunger, such that with the first locking means engaged with the annular lip the spring is held in compression;

the injector enclosure being of tubular construction and including an inwardly biased second locking means, the enclosure operably engaging the combination of the syringe and inner case within the enclosure, the canula and inner case extending from opposite ends of the injector enclosure respectively, the second locking means engaging the other end of the syringe body for locking the later in place at a forward position within the injector enclosure, so that as the inner case is drawn out of the enclosure, the plunger is drawn through the syringe body to fill the body with an injection liquid, the injector enclosure further including second disengaging means for forcing the first engagement means to disengage the annular lip of the inner case;

whereby with the canula positioned for injecting, the inner case is forced into the injector enclosure thereby driving the plunger into the body of the hypodermic syringe for injecting the injection liquid, until the first and second disengaging means are brought simultaneously into contact with the second and first locking means respectively, thereby disengaging the syringe body from the forward position within the injector enclosure, and the plunger from the annular lip of the inner case thereby allowing the spring to drive the hypodermic syringe fully into the injector enclosure to conceal the canula.

2. The combination retractable injector and injector enclosure of claim 1 wherein the plunger further includes a rod shaped element, the first locking means being a pair of opposed first tines disposed radially outwardly therefrom.

3. The combination retractable injector and injector enclosure of claim 2 wherein the first disengaging means is a coaxial annular torroidal element fixed to the rod shaped element and extending outwardly therefrom.

4. The combination retractable injector and injector enclosure of claim 2 wherein the grasping and manipulation means is a disk shaped element fixed at the end of the rod shaped element, the disk shaped element being of a diameter for snug fit within the inner case to compress the spring by contacting one end thereof.

5. The combination retractable injector and injector enclosure of claim 2 wherein the second locking means of the injector enclosure is a plurality of radially opposed second tines flexibly fixed to and radially inwardly extending from the injector enclosure.

6. The combination retractable injector and injector enclosure of claim 2 wherein the inner case includes an external annular lip, and further the injector enclosure includes an internal annular lip, the lips being mutually engaged in a forced fit at the outset of insertion of the inner case into the injector enclosure the lips touching at radiused annular lip surfaces for allowing the lips to pass each other, the lips, further, each having flat annular surfaces for mutual contact in preventing the inner case from being removed from the injector enclosure.

7. The combination retractable injector and injector enclosure of claim 2 wherein the second disengaging means is an annular rim positioned coaxially with respect to the plunger, the rim having a conical interior portion.

8. The combination retractable injector and injector enclosure of claim 7 wherein the first tines are curved in extension for smooth contact with the rim.

9. The combination retractable injector and injector enclosure of claim 7 wherein the injector enclosure includes at least one finger opening therein for accepting a finger in asserting finger pressure against the hypodermic syringe body to prevent the body from rotating when assembling the plunger to the sealing means.

* * * * *